(12) United States Patent
Scheir et al.

(10) Patent No.: US 7,459,694 B2
(45) Date of Patent: Dec. 2, 2008

(54) MOBILE GERMICIDAL SYSTEM

(75) Inventors: Robert Scheir, Sherman Oaks, CA (US); Robert Culbert, Manhattan Beach, CA (US)

(73) Assignee: Steril-Aire, Inc., Burbank, CA (US)

( * ) Notice: Subject to any disclaimer, the term of this patent is extended or adjusted under 35 U.S.C. 154(b) by 395 days.

(21) Appl. No.: 11/158,460

(22) Filed: Jun. 21, 2005

(65) Prior Publication Data

US 2006/0284109 A1 Dec. 21, 2006

(51) Int. Cl.
*A61L 2/10* (2006.01)
(52) U.S. Cl. .............................. 250/454.11; 250/494.1; 250/504 R; 422/24; 422/121
(58) Field of Classification Search ............ 250/455.11, 250/454.11, 494.1
See application file for complete search history.

(56) References Cited

U.S. PATENT DOCUMENTS

| | | | | |
|---|---|---|---|---|
| 2,273,449 | A | * | 2/1942 | Plishker .................... 250/494.1 |
| 2,757,305 | A | | 7/1956 | Dziergwa |
| 4,347,460 | A | | 8/1982 | Latassa |
| 5,144,146 | A | | 9/1992 | Wekhof |
| 5,151,135 | A | | 9/1992 | Magee |
| 5,225,000 | A | | 7/1993 | Fujii |
| 5,225,167 | A | | 7/1993 | Wetzel |
| 5,547,635 | A | | 8/1996 | Duthie, Jr. |
| 5,817,276 | A | | 10/1998 | Fencl |
| 5,891,399 | A | | 4/1999 | Owesen |
| 6,242,753 | B1 | * | 6/2001 | Sakurai ................... 250/504 R |
| 6,248,235 | B1 | | 6/2001 | Scott |
| 6,261,449 | B1 | | 7/2001 | Scott |
| 6,274,049 | B1 | | 8/2001 | Scott |
| 6,330,947 | B1 | | 12/2001 | Scott |
| 6,508,367 | B2 | | 1/2003 | Scott |

(Continued)

FOREIGN PATENT DOCUMENTS

DE 2356272 A * 5/1975

OTHER PUBLICATIONS

Nagy, Rudolph, Ph.D., "Application and Measurement of Ultraviolet Radiation", American Industrial Hygiene Assocation Journal, May-Jun. 1964, pp. 274-281, vol. 25.

(Continued)

*Primary Examiner*—Elizabeth L McKane
(74) *Attorney, Agent, or Firm*—SoCal IP Law Group LLP; Steven C. Sereboff; John E. Gunther (57) ABSTRACT

There is disclosed a mobile germicidal system and a process of decontaminating a wall and a ceiling of a room of undesirable substances. The system comprises a frame, a displacement device and an germicidal lamp. The displacement device is selected from the group comprising a wheel, a castor, a ball, a disk, a drum, a roller, and a traction belt. The displacement device is affixed to the frame. The germicidal lamp is affixed to the frame at a non-vertical incline. The process comprises providing a mobile germicidal system comprising an germicidal lamp having an enclosure having an exposed portion, at least a portion of the exposed portion disposed non-vertically and emitting ultraviolet radiation from the germicidal lamp at a wavelength substantially at 253.7 nm through all points in a horizontal area 6" directly above the mobile germicidal system while generating an insignificant quantity or less of ozone.

9 Claims, 8 Drawing Sheets

U.S. PATENT DOCUMENTS

| | | | |
|---|---|---|---|
| 6,524,457 | B1 | 2/2003 | Scott |
| 6,580,228 | B1 | 6/2003 | Chen |
| 6,656,424 | B1 | 12/2003 | Deal |
| 2003/0170152 | A1* | 9/2003 | Kobayashi et al. ....... 422/186.3 |
| 2004/0047776 | A1 | 3/2004 | Thomsen |
| 2004/0146437 | A1 | 7/2004 | Arts |

OTHER PUBLICATIONS

"Germicidal Ultraviolet Energy and Its Application", Bulletin FG66, Fuller Utraviolet Corp., Frankford, Illinois, prior art.

"Ultraviolet Air Purification", Specialized Ventilation Systems, Buffalo Missouri, prior art.

Latala, Adam and Radzik, W. Dr., "World Wide Test Studies Report Positive Effects of Germicidal U. V. on Eggs and Chicks", Applied Poultry Science, Inc., Agriculture Canada Research Station, Dept. of Veterinary Hygiene, 1993, Opole, Poland.

"Healthy Healthcare Facilities", Building Environment Report, vol. V, No. 7, Feb. 1997.

Ruegger, Urs P., "Entkeimung mit UV-C-Strahlen- Moglichkeiten und Grenzen", Separatdruck aus Swiss Med 7 (1985) Nr. 3b, Nov. 1984.

Sterilaire UV Lamps, prior art.

American Ultraviolet Company, "Mobile Room Sterilizer", Advertisement, Aug. 1992.

"Germicidal Ultraviolet Energy and Its Application", Bulletin FG66, Fuller Utraviolet Corp., Frankford, Illinois, date unknown.

"Ultraviolet Air Purification", Specialized Ventilation Systems, Buffalo Missouri, date unknown.

Sterilaire UV Lamps, date unknown.

* cited by examiner

MOBILE GERMICIDAL SYSTEM

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

BACKGROUND OF THE INVENTION

Office buildings, homes, factories, food preparation facilities, storage facilities and other structures often times are not well kept or go abandoned for periods of time. Many of these buildings are exposed to moisture due to climatic conditions, environmental conditions, floods, leaking roofs, failures in plumbing systems and other reasons. If a building is neglected, undesirable substances may accumulate on various surfaces including floors, walls and ceilings. Undesirable substances refer to any of mold, bacteria, fungi, viruses, mildew, allergens, spores, yeasts, mycotoxins, and endotoxins. As undesirable substances accumulate, they may become airborne within the structures.

Occupants of these buildings, such as hotel guests, students, office employees, and residents, may become ill. The occupants may become nauseated by foul odors emanating from the undesirable substances. The undesirable substances may render the room uninhabitable. Health is a factor for employee and student performance. More frequent illness results in increased medical costs for individuals. More frequent illness results in lost productivity for businesses.

DETAILED DESCRIPTION OF THE INVENTION

Throughout this description, the embodiments and examples shown should be considered as exemplars, rather than limitations on the apparatus and methods of the present invention.

Figure 1:
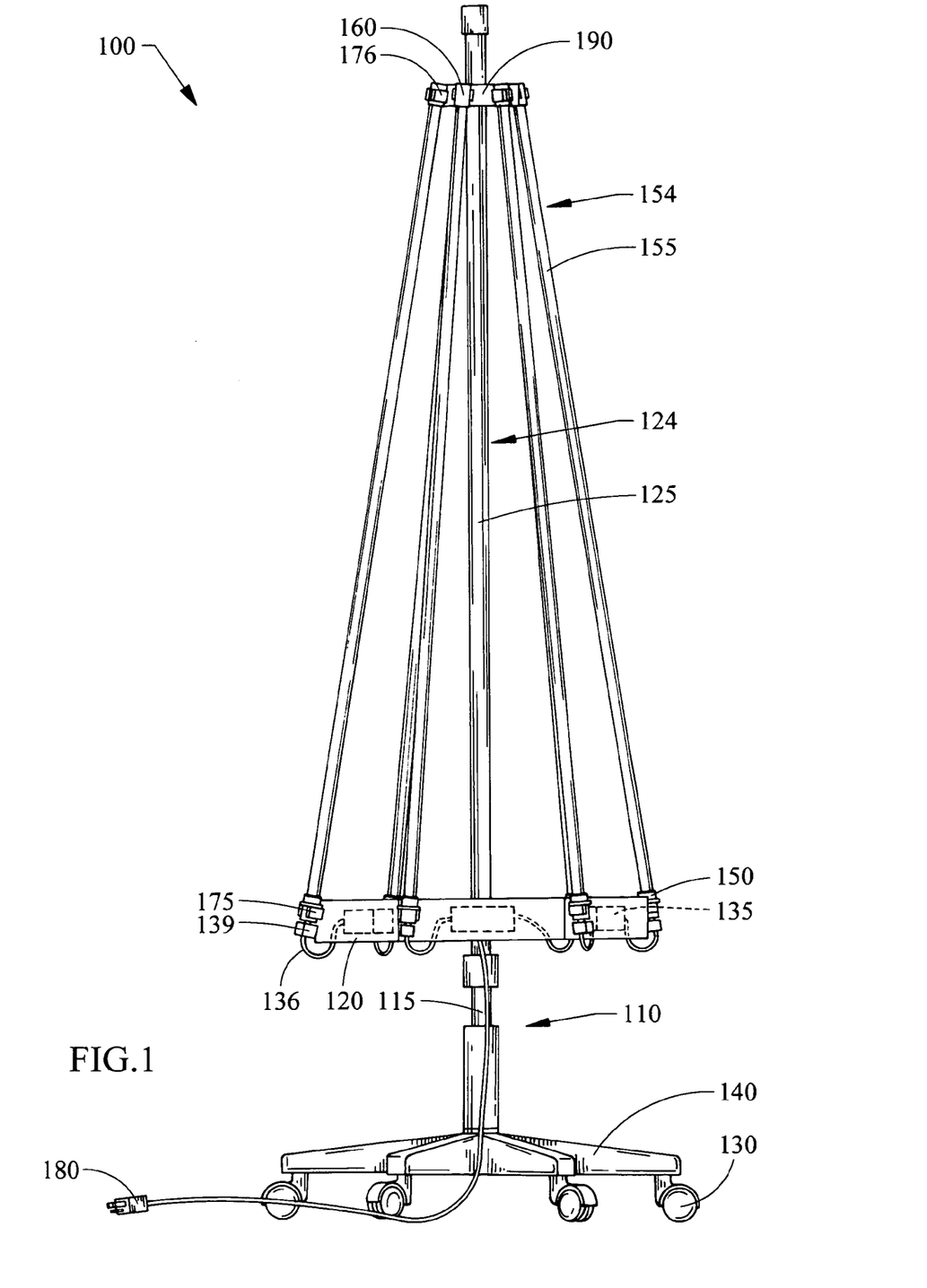
FIG. 1 is a perspective view of a mobile germicidal system.
Figure 2:
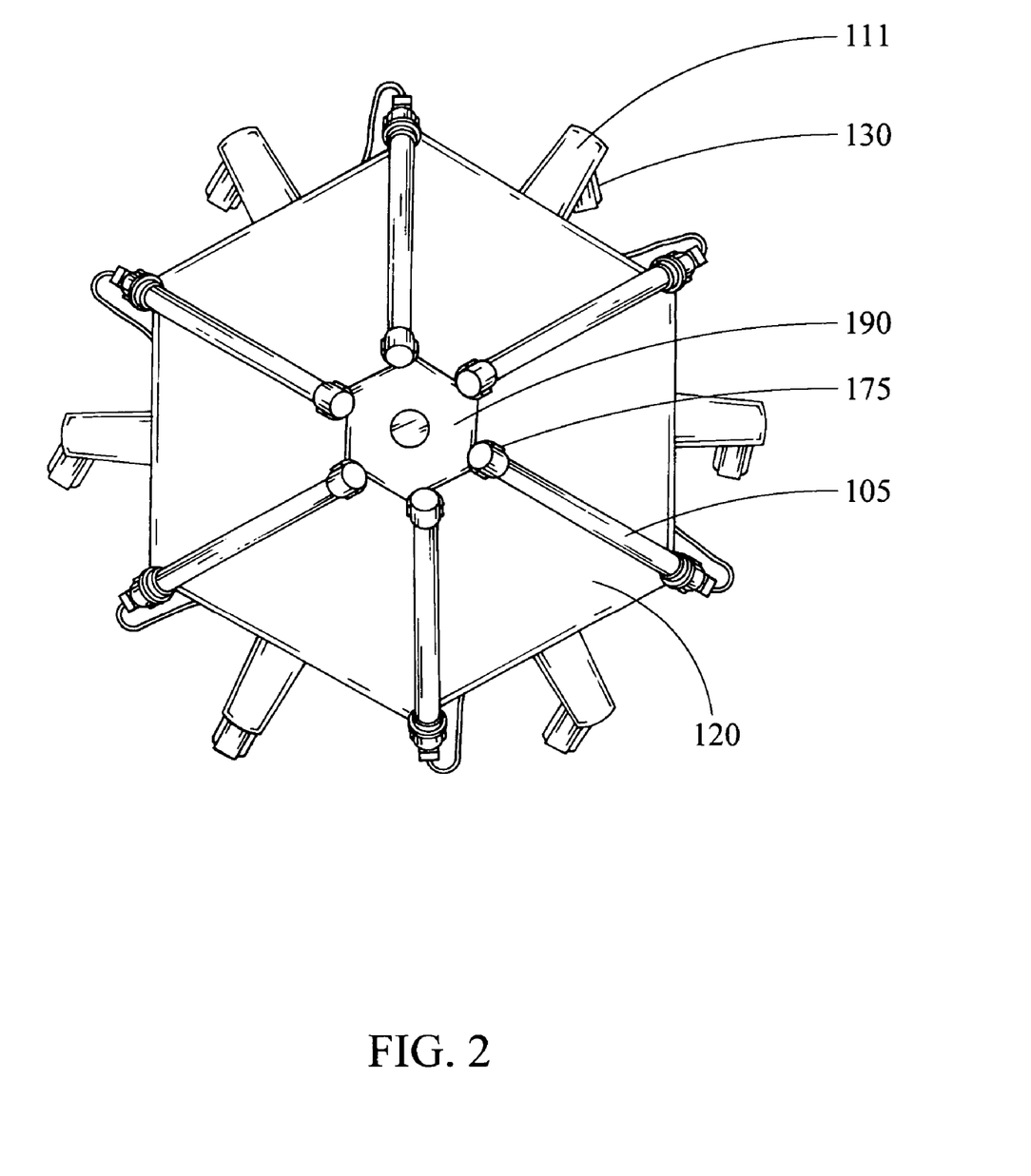
FIG. 2 is a plan view of a mobile germicidal system.

Referring now to FIG. 1 and FIG. 2, there are respectively shown a perspective and a plan view of a mobile germicidal system 100. The term mobile refers to the ability to being moved about readily. The term germicidal refers to the ability to retard the accumulation and/or kill undesirable substances. The mobile germicidal system 100 may be readily moved into, out of and within rooms or areas of a building or structure. The mobile germicidal system 100 may comprise one or a plurality of germicidal lamps 154, one or a plurality of sockets 139, a frame 124, one or a plurality of displacement devices 130 and one or a plurality of power supplies 135.

The term germicidal lamp refers to a device which emits radiation at a germicidal wavelength. A germicidal wavelength may be at an ultraviolet-C (UVC) wavelength. A germicidal wavelength, for example 254 nm, is a wavelength of light which retards buildup or accumulation of undesirable substances. UVC may also stun undesirable organisms.

Examples of germicidal lamps include electric discharge lamps and solid state devices. Solid state devices include light emitting diodes. Some deep ultraviolet light emitting diodes may emit light at a wavelength between 250 nm and 290 nm with a peak of 254 nm or other wavelengths. Deep ultraviolet light emitting diodes may be disposed in an array, for example a 4×4 array, a 10×10 array or other configuration.

The term electric discharge lamp refers to an apparatus which emits radiation caused by an electric discharge from electrodes in an enclosure. An electric discharge is electrical conduction through a gas or vapor in an applied electric field. An enclosure is a hollow device used to hold vaporizable materials and gases. An enclosure may be at least partially translucent. An enclosure may be constructed of glass, metal, quartz, plastic or other material. Examples of electric discharge lamps include fluorescent lamps, mercury vapor lamps, low pressure sodium lamps and high pressure sodium lamps.

For example purposes, the germicidal lamps 154 are shown as electric discharge lamps. The germicidal lamps 154 may each include an enclosure 155, a stem 150 and an end 160.

The stem 150 may be constructed of a ceramic, composite, plastic or other heat resistant and electrically non-conductive material. Typically, stems and ends of germicidal lamps are opaque or non-translucent. The stem 150 may include electrical contacts (not shown). The electrical contacts may be flush with, protrude out of, or be recessed within the stem 150. The electrical contacts may be electrically connected to electrodes (not shown).

The stem 150 may receive mechanical support from the frame 124 and electrical power from the socket 139. The stem 150 may attach to the socket 139 via industry standard pins such as a bi-pin, a single pin, a R17d, a medium bi-pin, a four pin, a 2G×13, a recessed double contact, a G–23, or a 2G–11. A single ended germicidal lamp typically includes a 4 pin circular base. The stem 150 may be a conduit for electrical components. The stem 150 may provide mechanical rigidity to the end of the germicidal lamp 150.

The dimensions and shape of the stem 150 may be selected based on the assembly size and weight constraints as well as power requirements. A common shape of a stem 150 is a substantially hollow cylinder with one end affixed to the enclosure 155. The stem 150 may have the geometry of a cube with beveled edges. The stem 150 may have a flange extending from the body of the cylinder. Common dimensions for a cylindrical stem include, but are not limited to, a length of approximately 1¼ inches, and a diameter of approximately ¾ of an inch. Common dimensions for a cubic stem include, but are not limited to, an edge length of ¾ of an inch.

The socket 139 may receive mechanical support from the stem 150. The socket 139 may provide power to the stem 150. The socket 139 may be constructed of metal, plastic, ceramic, glass, a composite or other material. The choice of material may be made based on the environment that the socket 139 will be exposed to. Examples of suitable materials for the socket 139 include, but are not limited to fiberglass, silica fiber, and ceramic.

A common socket for a germicidal lamp 150 may have a tombstone shape, and be approximately 1 inch in height, approximately 1 inch in width, and approximately $3/8^{th}$ inches in depth or other dimensions. The socket 139 may be similar in form to a cube with rounded edges having an edge length of approximately $1 3/8^{th}$ inches or other dimension. The socket 139 may take the form of a cylinder with a length of 2 inches and a diameter of $3/8^{th}$ of an inch or other dimensions.

The end 160 may be a second stem or an electrode-less mechanical support. Typical electric discharge lamps which are double ended include two stems. Typical electric discharge lamps which are single ended include one stem and one end. The end 160 may be constructed of metal, plastic, ceramic, glass, a composite or other material.

The germicidal lamp 154 may include a vaporizable material, such as mercury. The mercury, when electrically excited, may emit ultraviolet light at a germicidal wavelength. The ultraviolet light may pass through the enclosure 155. The ultraviolet light may be at least partially reflected, refracted and/or absorbed by the stem 150 and the end 160. The germicidal lamp 154 may be shaped toroidal, unshaped, cylindrical, bulbous or other shape. The germicidal lamp 154 may have a cross sectional shape of a circle, an oval, a tetrahedron, a pentagon, a hexagon, an octagon or other shape. Common cylindrical electric discharge lamps are manufactured in lengths of approximately 16", 22", 28", 34", 40" and other lengths.

The germicidal lamp 154 may be affixed to the frame 124 directly or indirectly. For example, the germicidal lamp 154 may be affixed to a fixture (not shown) which is in turn affixed to the frame 124.

The geometry and dimensions of the germicidal lamp 154 may be selected based on maximizing the direct exposure of the majority or entirety of the surfaces of a wall and/or a ceiling in a room to UVC. The longer and larger the germicidal lamp 154 is, the more surface area of a wall and a ceiling in a room will be directly exposed to UVC. The more surfaces of a room exposed to UVC, the more decontamination of undesirable substances may be effected. For example, the germicidal lamp 154 may be a 40" cylindrical single ended electric discharge lamp.

The term frame refers to a basic structural unit onto or into which other components of a system are fitted, to which they attach, or with which they are integrated. Frames are typically rigid. The frame 124 may include a first member 140, a second member 125, a third member 120 and a fourth member 190.

The first member 140 may be a pedestal or other structural member. A pedestal is the base of an upright structure. The first member 140 may be constructed of sheet metal, composites, plastic, wood or other material. For manufacturing cost savings, the first member 140 may be a pedestal of a manager's office chair. The first member 140 may have a geometry based on providing stability to an upright structure. The first member 140 may have the geometry of a triangle, a rectangle, a pentagon, a hexagon, an octagon or other shape.

Figure 7:
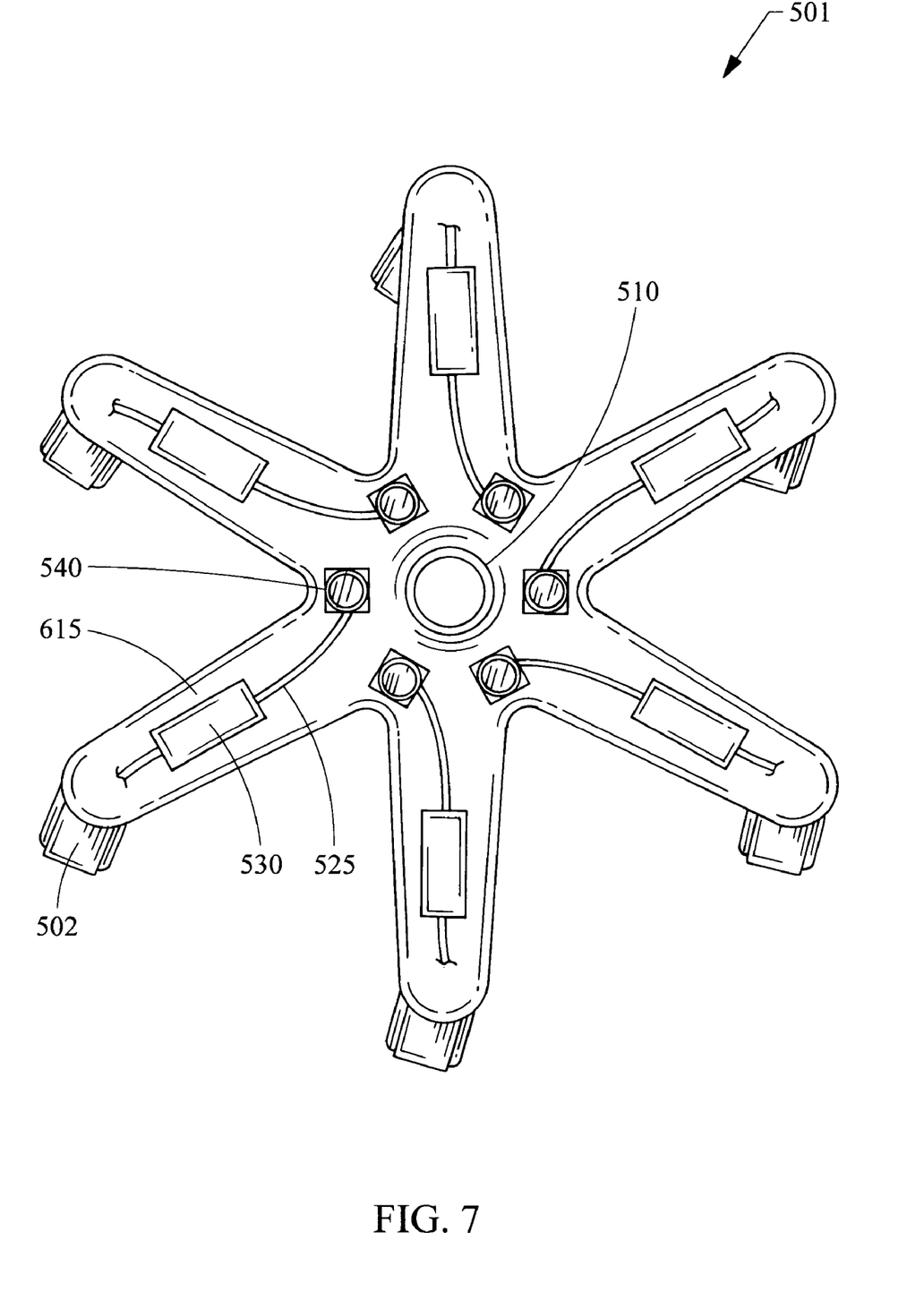
FIG. 7 is a plan view of a base of a mobile germicidal system.

The first member 140 may be disposed horizontally or at an inclination similar to a camera tripod. The first member 140 may be a plurality of radially disposed arms 615 coalescing at the center as shown in the plan view of FIG. 7. The radial length of the first member 140 may be selected based on a dimension less than ½ the width of a typical door opening in order that the mobile germicidal system 100 may pass through a door opening. The radial length of the first member 140 may be 12", 16" or other dimension.

The displacement device 130 may be affixed to the first member 140. The term affixed refers to any method of being physically attached or integrated, for example fastened, welded, chemically bonded, brazed, magnetically attached or other means for attachment. A displacement device refers to any device which allows a structure to be easily moved along a floor, ramp or other surface. Examples of displacement devices include wheels, castors, balls, disks, drums, roller and traction belts. The displacement device 130 may be in contact with the floor. The first member 140 may distribute the weight of the mobile germicidal system 100 to the floor via the displacement device 130. The mobile germicidal system 100 may be adapted to roll, slide or step along the floor, ground or ramp via the displacement device 130. The displacement device 130 may be selected based on the weight of the mobile germicidal system 100, the size of the mobile germicidal system 100 and the surfaces that the mobile germicidal system 100 may be displaced across. For example, the displacement device 130 may be a 2" diameter castor, a 4" diameter wheel or other device.

The second member 125 may be disposed vertically. The second member 125 may be a column, pillar, cylinder, mast, post, truss, spiral, coil, cone, pyramid, screw or other structural member. The second member 125 may have a cross section of a circle, square, triangle or other shape. The second member 125 may be solid or hollow. The second member 125 may be constructed of metal, a composite, wood or other material. The cross sectional dimensions of the second member 125 may be selected based upon the objects which it may support. For example, the second member 125 may have a cross sectional diameter of 2", 3" or other dimension.

The second member 125 may be affixed to or integral with the first member 140. The second member 125 may receive mechanical support from the first member 140. The second member 125 may have a height based on the mobile germicidal system 100 being shorter than the height of a typical door opening or shorter than a typical ceiling of a room. The height of the second member 125 may be selected based on positioning the germicidal lamp 154 close to the ceiling of a room.

UVC radiation intensity is related to the proximity to the source of the UVC emission, the germicidal lamp 154. Thus, the closer the germicidal lamp 154 is to the ceiling, the greater intensity of UVC the ceiling will be exposed to. The second member 125 may have a fixed height or may have a variable height determined by a telescoping means, a screw means or other means for vertical displacement. For example, the height of the second member 125 may be 38", 56", 76" or other dimension.

Figure 3:
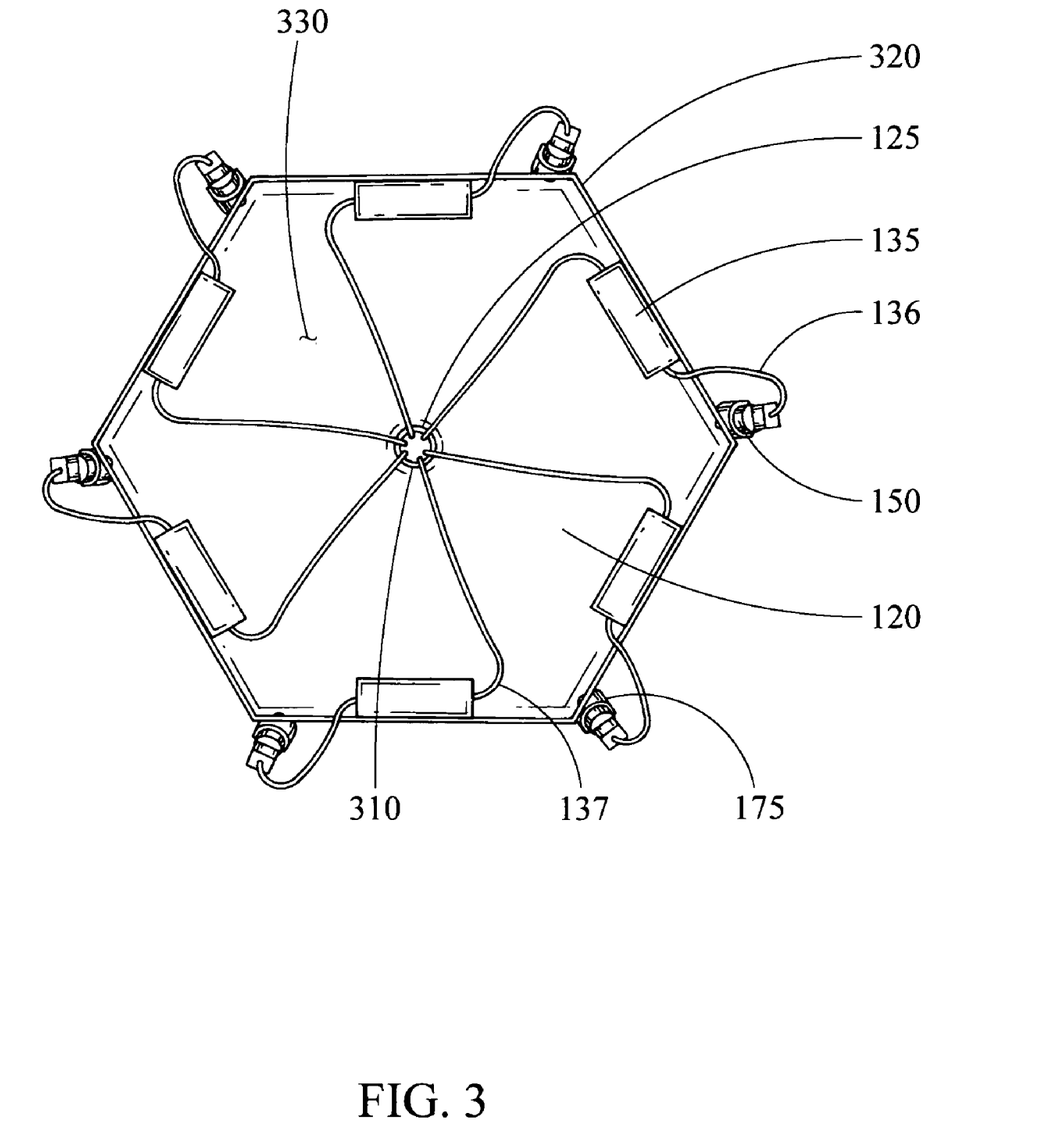
FIG. 3 is a plan view of a base of a mobile germicidal system.

The third member 120, also shown in the plan view of FIG. 3, may be a base, mount or foundation. A base is a part of a frame or structure on to or in to which operating parts of a system are affixed. The third member 120 may be constructed from metal, composites, wood or other material. The third member 120 may be affixed to or integral with the second member 125. The third member 120 may be disposed horizontally or at an inclination. The third member 120 may provide mechanical support to the germicidal lamp 154. The geometry of the third member 120 may be selected based on offsetting the stem 150 of the germicidal lamp 154 horizontally from the second member 125. The geometry of the third member 120 may be selected based on a dimension less than the width of a typical opening of a door in order for the mobile germicidal system 100 to readily pass through the door opening. The geometry of the third member 120 may be selected based on the size of one or a plurality of power supplies 135, which in turn may be affixed to the third member 120. The third member 120 may have a cross sectional shape of a circle, triangle, rectangle, pentagon, hexagon, or other regular or irregular shape. For example purposes, the third member 120 may have the cross sectional geometry of a regular hexagon with an edge length of 10", 12" or other length.

The third member 120 may define an opening 310 through which the second member 125 is disposed. The opening 310 may have a cross sectional shape based on the cross sectional shape of the second member 125. The third member 120 may be adapted to be displaced vertically along the second member 125. The vertical position of the third member 120 relative to the second member 125 may be selected based on a desired elevation of the stem 150 of the germicidal lamp 154. The third member 120 may be disposed relative to the second member 125 at a height approximately 24", 36", 48" or other dimension above the ground. The higher the third member 120 is disposed relative to the second member 125, the closer the germicidal lamp 154 may be disposed relative to the ceiling of a room, thus concentrating UVC towards the ceiling.

The third member 120 may include one or a plurality of clasps 175. The clasp 175 may provide mechanical support to the stem 150 of the germicidal lamp 154. The clasp 175 may be integral to or be affixed to the third member 120. The clasp 175 may take the form of one of or combinations of a spring clamp, a sleeve, a hanger, a race, a locking clamp, a clip, a holster, and a strap. The clasp 175 may comprise a material that is resistant to heat and environmental elements.

An example of the clasp 175 is a stamped aluminum spring clip with a hard plastic coating. The clasp 175 of FIG. 1 is a common spring clip which may secure a $\frac{3}{4}^{th}$ inch diameter germicidal lamp. The common spring clip may have bent surfaces that contact the stem 150 and/or the enclosure 155 of the germicidal lamp 154 in 30 degree arcs or other dimension, $\frac{5}{8}^{th}$ of an inch in width or other dimension, on opposite sides of the germicidal lamp 154. Another example of the clasp 175 is a composite rigid sleeve. Moreover, the clasp 175 may be a stainless steel locking clamp with neoprene teeth.

The clasp 175 may be disposed relative to the third member 120 at or near an edge 320 of the third member 120. The clasp 175 may be disposed relative to the third member 120 at or near a position 330 that is located approximately ½ the distance between the edge 320 and the opening 310 or at another position. The position where the clasp 175 is affixed to or integral with the third member 120 may be selected based on horizontally offsetting the stem 150 of the germicidal lamp 154 from the second member 125. The stem 150 of the germicidal lamp 154 may be horizontally offset from the second member 125 by 10", 12", 13" or other dimension. The greater the horizontal offset of the stem 150 from the second member 125, the more spread out across the surfaces of the room UVC will be emitted.

A power supply is an electronic device or system that converts electric power from a form being received to a form which is supplied to a load. A power supply may convert power from DC to AC, from DC to DC, or from AC to DC, or other. A power supply may regulate electric power. The power supply 135 may be or include a ballast. A ballast is a power converter that regulates electric power and functions as a starting and control unit for an electric discharge device. The ballast initially provides a voltage to ionize the gas or vaporizable material in the tube. The ballast then controls the power that drives the germicidal lamp 154.

The power supply 135 or a plurality of power supplies 135 may be partially or fully affixed to, mounted to or integral with the third member 120 (as shown in FIG. 1), the second member 125, the first member 140 (not shown), the fourth member 190 (not shown) or remote from the mobile germicidal system 100 (not shown). The power supply 135 may be partially or fuly integral to the germicidal lamp 154. The power supply 135 may receive power from a generator (not shown), household current via wires and a plug 180, a battery pack (not shown) or another power source. The power supply 135 may provide power to a single germicidal lamp 154 or a plurality of germicidal lamps 154. The power supply 135 may provide power to the stem 150 of the germicidal lamp 154 via wires 136 and the socket 139.

Figure 4:
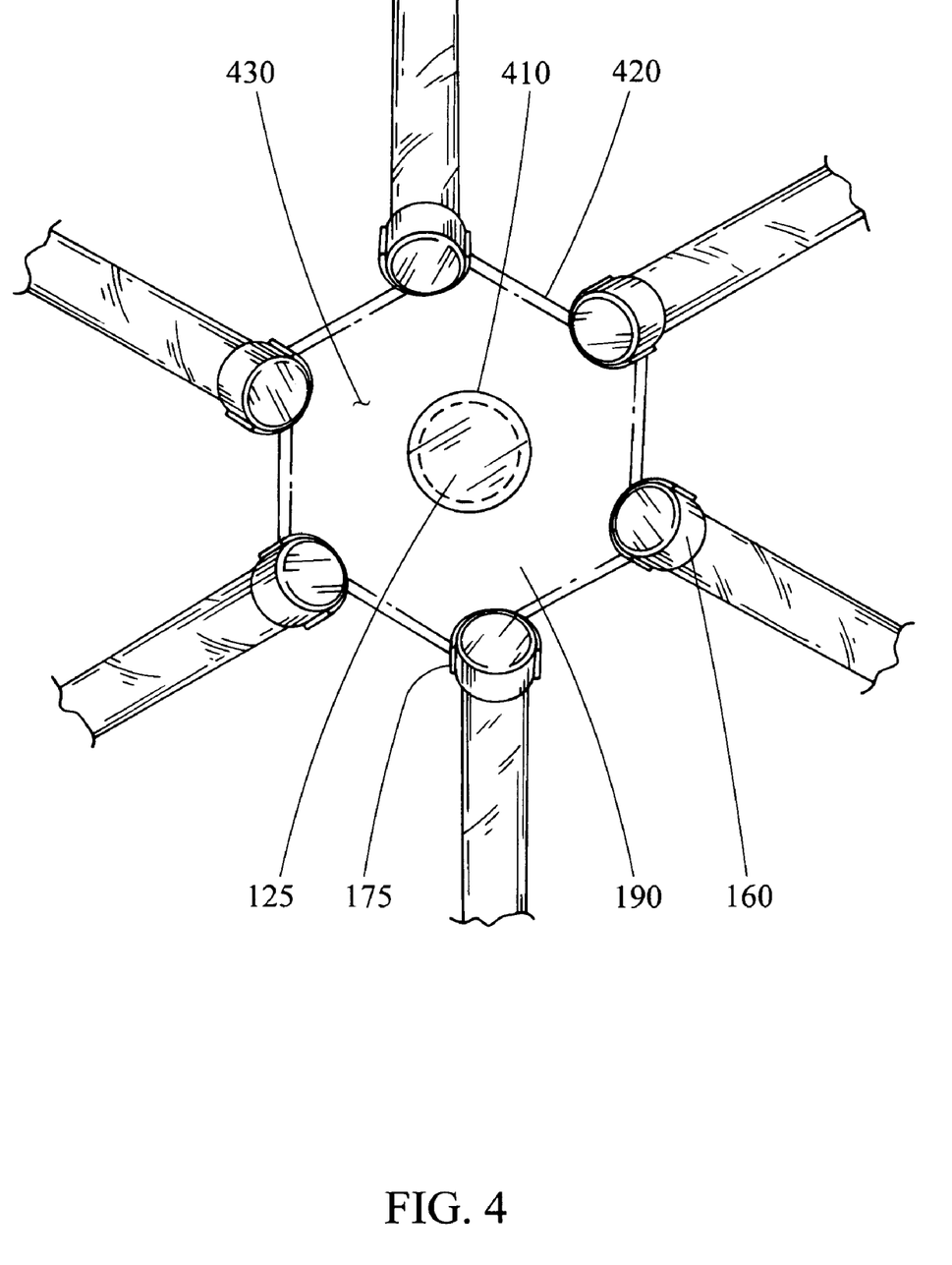
FIG. 4 is a plan view of a mount of a mobile germicidal system.

The fourth member 190, also shown in the plan view of FIG. 4, may be a base, mount or foundation. The fourth member 190 may be affixed to or integral with the second member 125. The fourth member 190 may be disposed horizontally or at an inclination. The fourth member 190 may provide mechanical support to the germicidal lamp 154. The fourth member 190 may be constructed of metal, composite, wood or other material. The geometry of the fourth member 190 may have the shape of a circle, square, hexagon or other regular or irregular shape. The geometry of the fourth member 190 may be selected based on offsetting the end 160 of the germicidal lamp 154 horizontally from the second member 125. The dimensions of the fourth member 190 may be selected based on offsetting the end 160 of the germicidal lamp 154 from the second member 125 a different distance than the offset of the stem 150 of the germicidal lamp 154 from the second member 125. For example, the fourth member 190 may have a substantially circular shape with an outer diameter of 5, 6, 7 inches or other dimension.

The fourth member 190 may define an opening 410 through which a portion of the second member 125 is disposed. The fourth member 190 may include a clasp 176. The clasp 176 may be integral with or affixed to the fourth member 190. The clasp 176 may be affixed to or integral with the fourth member 190 at an edge 420 of the fourth member 190. The clasp 176 may be affixed to or integral with the fourth member 190 at a position 430 which is ¾ of the distance from the opening 410 to the edge 420 or other position. The clasp 176 may provide mechanical support to the end 160 of the germicidal lamp 154. Thus, the end 160 of the germicidal lamp 154 may be horizontally offset 3", 4" or other dimension from the second member 125.

Typical stems and ends of germicidal lamps are not considered to be translucent to UVC. In general, UVC is not emitted in substantial quantities through either the stem or the end. In typical germicidal systems when UVC is being emitted, a shadow may result beyond the stem and/or the end. If all the germicidal lamps of a germicidal system are disposed vertically, a shadow may be formed in a horizontal plane above the germicidal lamps. If UVC does not emit on a given area, for example a ceiling, due to a shadow effect from the stem or ends of the germicidal lamps, undesirable substances on the ceiling may continue to accumulate.

If the horizontal offset between the stem 150 and the second member 125 is different than the horizontal offset between the end 160 and the second member 125, then the germicidal lamp 154 will be disposed at a non-vertical incline relative to the floor. An incline is an upward or downward slant or grade forming an angle with the horizon. The term incline may include a decline. An exposed portion of the enclosure 155 of the germicidal lamp 154 is the portion of the enclosure 155 which is not surrounded by either the stem 150 or the end 160. If the germicidal lamp 154 is disposed at a non-vertical incline relative to the floor, then at least an exposed portion of the enclosure 155 may be disposed non-vertically.

When the mobile germicidal system 100 is receiving power and operating, the germicidal lamp 154 may emit UVC radiation towards the walls and the ceiling of a room. UVC may be emitted omnidirectionally through the exposed portion of the enclosure 155. If at least an exposed portion of the enclosure 155 is disposed non-vertically, UVC may be emitted vertically and in directions having both vertical and horizontal components. When the operating germicidal lamp 154 is disposed at a non-vertical incline relative to the horizon, UVC will be emitted towards the ceiling above the germicidal lamp 154.

If the mobile germicidal system 100 includes at least two germicidal lamps 154 disposed non-parallel to each other, the germicidal lamps may emit UVC radiation through all points in a horizontal area 6" directly above the mobile germicidal system 100. Depending on the incline of the germicidal lamps, the germicidal lamps may emit UVC radiation through all points in a horizontal area 1", 3", 4" or other dimension directly above the mobile germicidal system. The incline of the germicidal lamps may determine at what height above the mobile germicidal system that no shadow exists. A mobile germicidal system 100 may include at least two germicidal lamps 154 disposed not parallel to each other wherein the germicidal lamps are disposed in a conical arrangement, V-shape arrangement, diamond arrangement, pyramid arrangement, or other arrangement. By operating a mobile germicidal system 100 where the germicidal lamps 154 are disposed at a non-vertical incline UVC may be emitted both towards the ceiling and towards the walls providing extensive exposure of a room's surfaces to UVC without shadows on the ceilings or walls.

As accumulation of undesirable substances within such structures is reduced or minimized, employee and student performance may be improved, health care costs may be saved and productivity may be increased. Moreover, if uninhabitable spaces are decontaminated, uninhabitable areas may become habitable for work, storage, business, food preparation, manufacturing, residence and other purposes.

Additional methods of cleaning walls and ceilings include applying chemicals, often times via high pressure sprayers. Such chemicals may emanate toxic fumes may be dangerous enough that the entire building must be vacated. With the mobile germicidal system 100, only one room may be vacated at a time.

Figure 5:
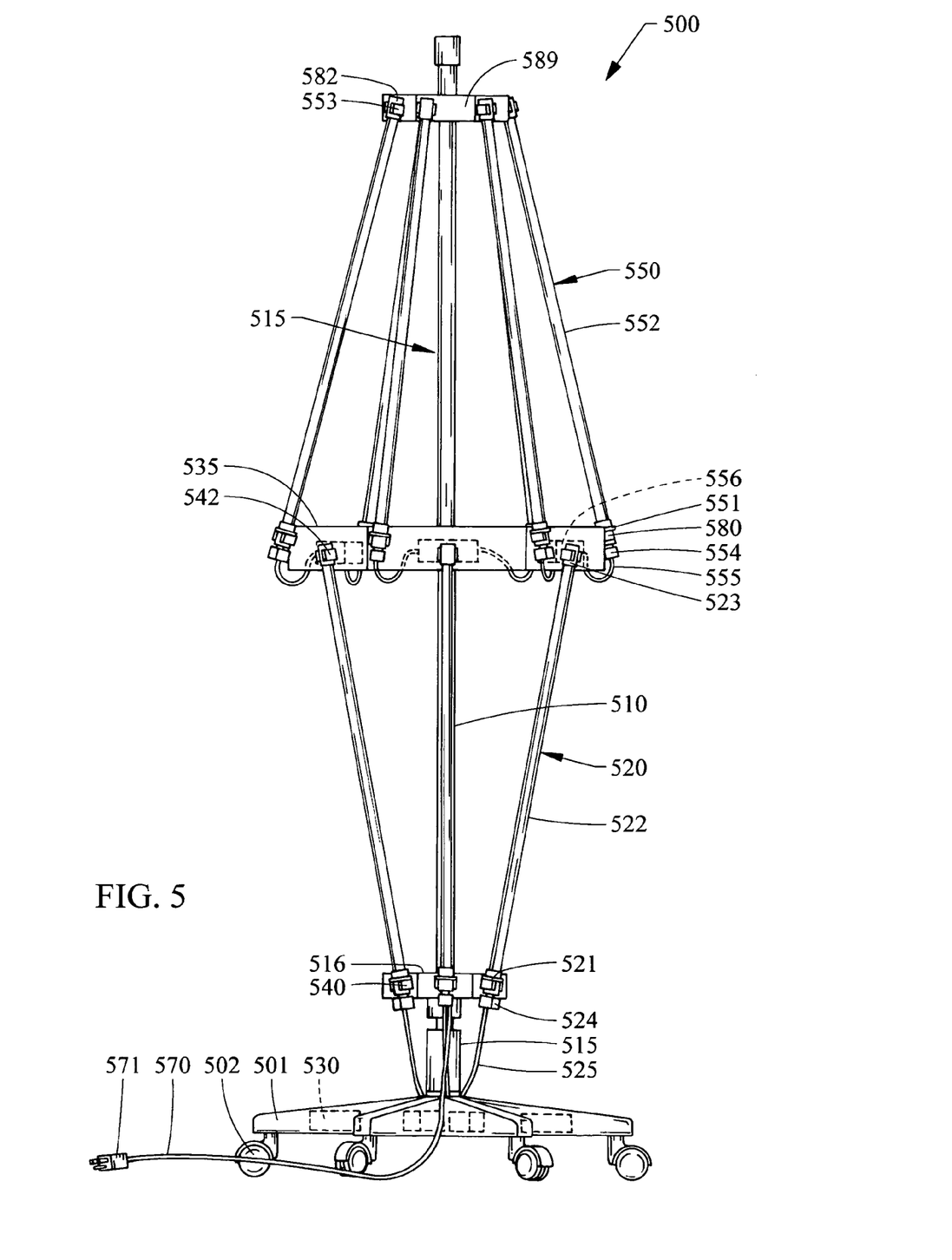
FIG. 5 is a perspective view of a base of a mobile germicidal system.

Referring now to FIG. 5, there is shown a perspective view of a mobile germicidal system 500. The mobile germicidal system 500 may include a fixture 515, a first plurality of germicidal lamps 520, a second plurality of germicidal lamps 550, a first plurality of power supplies 530, a second plurality of power supplies 556 and a displacement device 502. The mobile germicidal system 500 of FIG. 5 may be configured with the first plurality of germicidal lamps 520 disposed at a lower position than the second plurality of germicidal lamps 550. By including a first plurality of germicidal lamps 520 and a second plurality of germicidal lamps 550, a larger surface area of the walls, floor and ceiling of a room may be exposed to UVC while the mobile germicidal system 500 is operating. By exposing more surfaces of a room to UVC, the mobile germicidal system 500 may not need to be moved horizontally and vertically around the room or operate within the room. Moreover, decontamination time may be reduced.

The fixture 515 may include a pedestal 501, a column 510, a first base 516, a second base 535, a third base 589 and a plurality of castors 502. The pedestal 501, the first base 516, the second base 535 and the third base 589 may be affixed to or integral with the column 510. The castors 502 may be affixed to or integral with the pedestal 501.

The first plurality of germicidal lamps 520 may each include a stem 521, an enclosure 522 and an end 523. The stem 521 may receive electrical power from a socket 524. The socket 524 may be electrically connected to one or a plurality of the first plurality of power supplies 530 via wires 525.

The second plurality of germicidal lamps 550 may each include a stem 551, an enclosure 552 and an end 582. The stem 551 may receive electrical power from a socket 554. The socket 554 may be electrically connected to one or a plurality of the second plurality of powers supplies 556 via wires 555.

The first plurality of power supplies 530 and the second plurality of power supplies 556 may be electrically connected to a power source (not shown) via wires 570 and a plug 571, socket (not shown) or other device.

Figure 6:
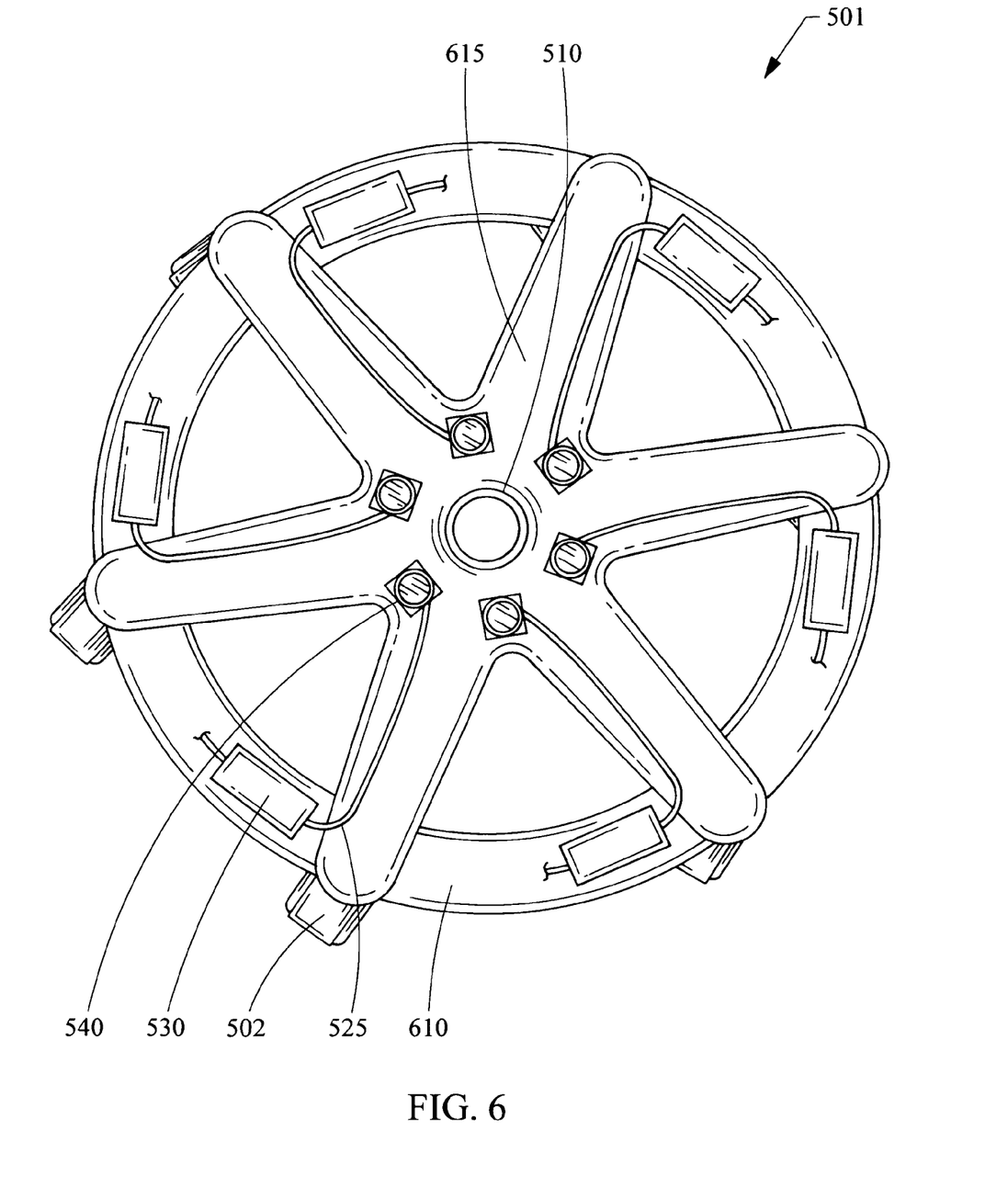
FIG. 6 is a plan view of a base of a mobile germicidal system.

The pedestal 501, also shown in the plan view of FIG. 6, may include a plurality of concentric radially extending members 615 and a circular shaped member 610 encompassing the outermost portions of the radially extending members 615. The plurality of concentric radially extending members 615 may be affixed to or integral with the circular shaped member 610. The outer diameter of the circular shaped member 610 may be based on the length of the plurality of the radially extending members 615. The inner diameter of the circular shaped member 610 may be based on a dimension such that the distance between the inner diameter of the circular shaped member 610 and the outer diameter of the circular shaped member 610 is larger than the dimensions of the power supply 530. The plurality of power supplies 530 may be affixed to or integral with the circular shaped member 610 or the radially extended arms (as shown in the plan view of a pedestal of FIG. 7). The location where to dispose the plurality of power supplies 530 may be based on providing horizontal stability to the mobile germicidal system 500.

The column 510 may have a length selected based on a dimension less than the typical height of a ceiling of a room. The column 510 may have a length greater than the length required to support a first plurality of germicidal lamps 520 and a second plurality of germicidal lamps 550 wherein the first plurality of germicidal lamps 520 is disposed below the second plurality of germicidal lamps 520. For example, if each germicidal lamp is a 40" lamp disposed at a 68 degree vertical incline (as shown for the second plurality of germicidal lamps 550 in FIG. 5) or decline (as shown for the first plurality of germicidal lamps 550 in FIG. 5), the vertical component of the germicidal lamp would be approximately 38". Thus, the minimum length of the column may be selected as two times 38" (76") or other dimension, for example 84".

The first base 516 may include a plurality of clasps 540. The plurality of clasps 540 may provide mechanical support to the stems 521. The plurality of clasps 540 may horizontally offset the stems 521 a first distance from the column 510.

The second base 535 may include a first plurality of clasps 542. The first plurality of clasps 542 may provide mechanical support to the ends 523. The first plurality of clasps 542 may horizontally offset the ends 523 a second distance from the column 510. The second base 535 may include a handle (not shown). A person moving mobile germicidal system 500 may hold the mobile germicidal system 500 by the handle. A person may tip the mobile germicidal system 500 via the handle in order to fit the mobile germicidal system 500 through a standard 6 foot 8 inch high doorway. By holding the mobile germicidal system 500 via the handle while displacing the mobile germicidal system 500, it is less likely that the mobile germicidal system 500 will tip over causing the electric discharge lamps 520, 550 to break.

If the first plurality of clasps 542 horizontally offsets the ends 523 a greater distance from the column 510 than the plurality of clasps 540 horizontally offsets the stems 521 from the column, then the first plurality of germicidal lamps 520 may be disposed at a vertical decline. If the first plurality of clasps 542 horizontally offsets the ends 523 a lesser distance from the column 510 than the plurality of clasps 540 horizontally offsets the stems 521 from the column, then the first plurality of germicidal lamps 520 may be disposed at a vertical incline (not shown). If the first plurality of germicidal lamps 520 are disposed at a vertical incline or decline then a UVC shadow on the floor or a horizontal plane below the first plurality of germicidal lamps 520 may be minimized.

The second base 535 may provide mechanical support to the second plurality of power supplies 556.

The second base 535 may include a second plurality of clasps 580. The second plurality of clasps 580 may provide mechanical support to the stems 551. The second plurality of clasps 580 may horizontally offset the stems 551 a third distance from the column 510.

The third base 589 may include a plurality of clasps 553. The plurality of clasps 553 may provide mechanical support to the ends 582. The plurality of clasps 553 may horizontally offset the ends 582 a fourth distance from the column 510.

If the second plurality of clasps 580 horizontally offsets the stems 551 a different distance from the column 510 than the plurality of clasps 553 offsets the ends 582, then the second plurality of germicidal lamps 550 may be disposed at a slope or gradient relative to the horizon. If the second plurality of germicidal lamps 550 are disposed at a slope or gradient relative to the horizon, then a UVC shadow on the ceiling or a horizontal plane above the second plurality of germicidal lamps 550 may be minimized.

Figure 8:
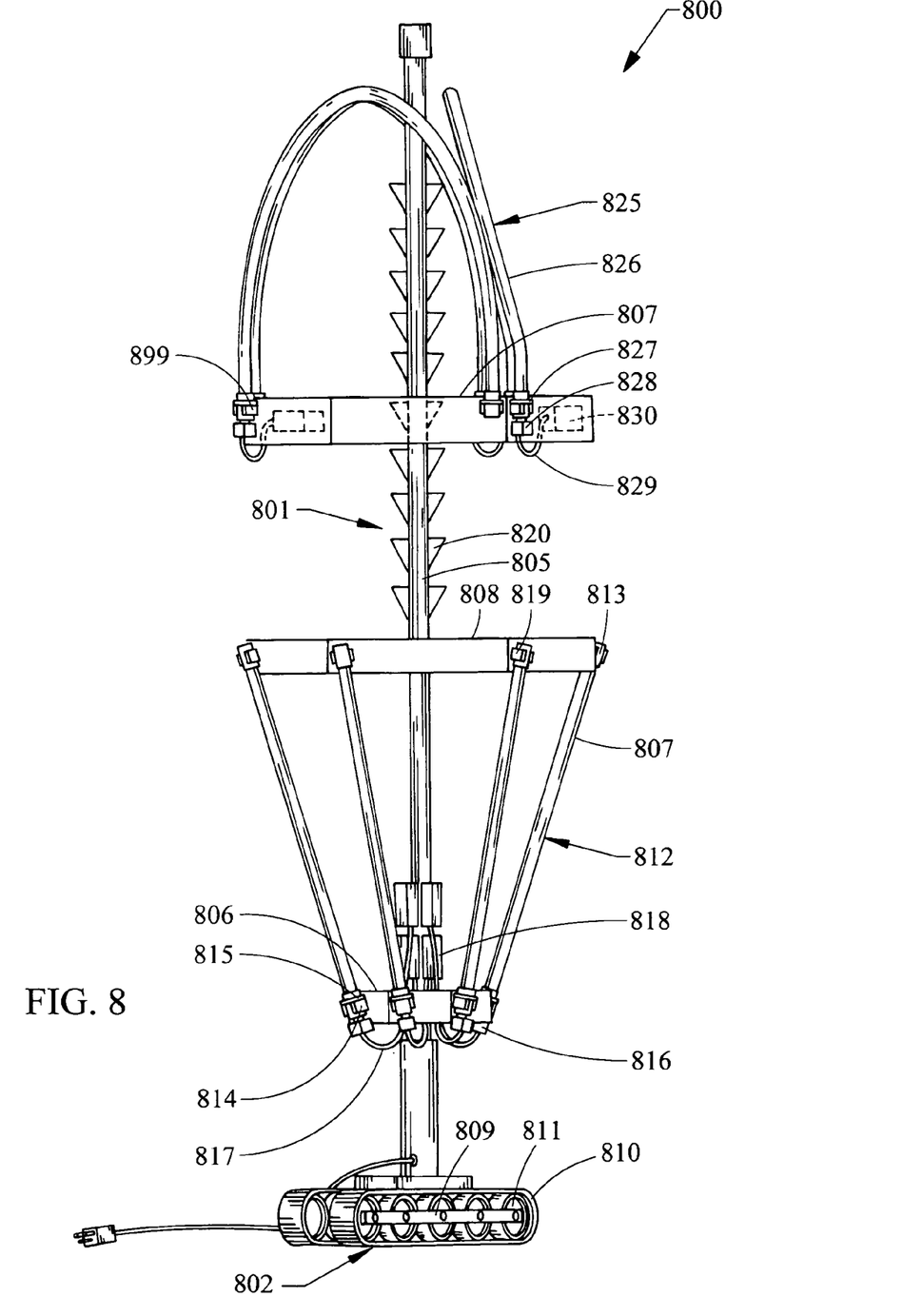
FIG. 8 is a perspective view of a mobile germicidal system.

Referring now to FIG. 8, there is shown a mobile germicidal system 800. The mobile germicidal system 800 may include a frame 801, a first plurality of germicidal lamps 812, a second plurality of germicidal lamps 825, a first plurality of power supplies 818, a second plurality of power supplies 830 and a displacement device 802. The mobile germicidal system 800 may be configured so that at least one of the plurality of germicidal lamps may be reconfigured to different heights.

The frame 801 may include a pedestal 809, a first base 806, a second base 808, a third base 807 and a column 805. The pedestal 809, the first base, the second base 808 and the third base 807 may be affixed to or integral with the column 805.

The first plurality of germicidal lamps 812 may each include a stem 815, an end 813 and an enclosure 807. The stem 815 may receive electrical power via a socket 816. The socket 816 may be electrically connected to one or a plurality of the first plurality of power supplies 818. One or a plurality of the first plurality of power supplies 818 may be affixed to or integral with the column 805.

The second plurality of germicidal lamps 825 may each include two stems 827 and an enclosure 826. The enclosure 826 may be a U-shaped enclosure. The U-shaped enclosure has at least a portion of the enclosure disposed horizontally. Thus, the germicidal lamp 825 may emit at least some UVC vertically towards the ceiling of a room. At least one of the stems 827 of each germicidal lamp 825 may receive electrical power from the socket 828. The socket 828 may be electrically connected to one or a plurality of the second plurality of power supplies 830. One or a plurality of the second plurality of power supplies 830 may be affixed to or integral with the third base 807 or the column (not shown). One or a plurality of the second plurality of power supplies 830 may be integrated with the germicidal lamps 825.

The first base 806 may include one or a plurality of clasps 814. The clasps 814 may provide mechanical support to the stems 815. The second base 805 may include one or a plurality of clasps 819. The clasps 819 may provide mechanical support to the ends 813. The third base 807 may include one or a plurality of clasps 899. The clasps 899 may provide mechanical support to the stems 827.

The column 805 may include one or a plurality of stops 820. The stops 820 may be a protrusion, nub or other mechanical device which vertically fixes a base relative to a column. The stops 820 may be retractable into the column 805 such that the third base 807 may be raised or lowered relative to the column 805. The third base 807 may include a lift (not shown) which aids the third base 807 in being raised or lowered relative to the column 805. Common lifts include a crane, an elevator, a hoist, a jack, a telescoping member, and a trestle. If the third base 807 may be lowered relative to the column 805, the mobile germicidal system 800 may readily pass through a doorway without needing to be tilted. If the third base 807 may be raised relative to the column 805, the second plurality of germicidal lamps 825 may be positioned proximate to the ceiling of a room.

The displacement device 802 may be affixed to or integral with the pedestal 809. The displacement device 802 shown in FIG. 8 is a tractor style displacement device. The displacement device 802 may include a plurality of wheels 811 and a track 810. Tracks may be constructed of metal, composites, rubber or other durable materials. Tracks allow the weight of the mobile germicidal system 800 to be distributed over a greater surface area than wheels and prevent the mobile germicidal system 800 from sinking into a surface such as mud, dirt or sand. Since some buildings have no manufactured flooring, the mobile germicidal system 800 may be displaced along an earthen surface via the track 810.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

CLOSING COMMENTS

The foregoing is merely illustrative and not limiting, having been presented by way of example only. Although exemplary embodiments of the invention have been shown and described, it will be apparent to those having ordinary skill in the art that changes, modifications, and/or alterations may be made, none of which depart from the spirit of the present invention. All such changes, modifications and alterations should therefore be seen as within the scope of the present invention.

Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

For any means-plus-function limitations recited in the claims, the means are not intended to be limited to the means disclosed herein for performing the recited function, but are intended to cover in scope any means, known now or later developed, for performing the recited function.

As used herein, "plurality" means two or more.

As used herein, a "set" of items may include one or more of such items.

As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, "and/or" means that the listed items are alternatives, but the alternatives also include any combination of the listed items.

It is claimed:

1. A mobile germicidal system, comprising:
   a frame comprising two bases, the two bases vertically separated from each other
   a displacement device selected from the group comprising a wheel, a castor, a ball, a disk, a drum, a roller, and a traction belt, the displacement device affixed to the frame
   two pluralities of elongate cylindrical electric discharge germicidal lamps, each plurality of germicidal lamps affixed to the respective base, wherein at least one of the two pluralities of germicidal lamps is disposed in a conical arrangement.

2. The mobile germicidal system of claim 1, wherein the frame comprises a lift selected from the group comprising a crane, an elevator, a hoist, a jack, a telescoping member, and a trestle, the plurality of germicidal lamps affixed to the lift, one of the two bases affixed to the lift.

3. The mobile germicidal system of claim 2, wherein the lift is a telescoping member.

4. The mobile germicidal system of claim 1, wherein the two pluralities of germicidal lamps are adapted to emit radiation through all points in a horizontal area 6" directly above the mobile germicidal system.

5. A mobile germicidal system, comprising:
   a frame comprising two bases, the two bases vertically separated from each other
   a displacement device selected from the group comprising a wheel, a castor, a ball, a disk, a drum, a roller, and a traction belt, the displacement device affixed to the frame
   two pluralities of elongate cylindrical electric discharge germicidal lamps, each plurality of germicidal lamps affixed to the respective base
   wherein
      the germicidal lamps within each plurality of germicidal lamps are not parallel to each other
      one of the two bases is vertically adjustable relative to the other one of the two bases.

6. The mobile germicidal system of claim 5, wherein the plurality of germicidal lamps are adapted to emit radiation through all points in a horizontal area 6" directly above the mobile germicidal system.

7. The mobile germicidal system of claim 5, wherein the frame comprises a lift selected from the group comprising a crane, an elevator, a hoist, a jack, a telescoping member, and a trestle, one of the two bases affixed to the lift.

8. The mobile germicidal system of claim 7, wherein the lift is a jack.

9. The mobile germicidal system of claim 5, wherein
   the two pluralities of germicidal lamps adapted to emit radiation through all points in a horizontal area 6" directly above the mobile germicidal system
   the frame comprises a telescoping member, one of the two bases affixed to the telescoping member.

* * * * *